United States Patent
Mercati et al.

(10) Patent No.: US 10,953,066 B2
(45) Date of Patent: Mar. 23, 2021

(54) COMPOSITIONS FOR THE TREATMENT OF CHRONIC ULCERS

(71) Applicant: ABOCA S.P.A. SOCIETÀ AGRICOLA, Sansepolcro (IT)

(72) Inventors: Valentino Mercati, Sansepolcro (IT); Anna Maidecchi, Sansepolcro (IT)

(73) Assignee: ABOCA S.P.A. SOCIETÀ AGRICOLA, Sansepolcro (IT)

( * ) Notice: Subject to any disclaimer, the term of this patent is extended or adjusted under 35 U.S.C. 154(b) by 49 days.

(21) Appl. No.: 14/396,202

(22) PCT Filed: Apr. 23, 2013

(86) PCT No.: PCT/IB2013/053190
§ 371 (c)(1),
(2) Date: Oct. 22, 2014

(87) PCT Pub. No.: WO2013/160824
PCT Pub. Date: Oct. 31, 2013

(65) Prior Publication Data
US 2015/0110888 A1  Apr. 23, 2015

(30) Foreign Application Priority Data
Apr. 23, 2012 (IT) .......................... RM2012A000174

(51) Int. Cl.
| | | |
|---|---|---|
| *A61K 36/00* | (2006.01) | |
| *A61K 36/886* | (2006.01) | |
| *A61K 36/77* | (2006.01) | |
| *A61K 36/87* | (2006.01) | |
| *A61K 35/644* | (2015.01) | |
| *A61K 36/23* | (2006.01) | |
| *A61K 36/38* | (2006.01) | |
| *A61K 36/896* | (2006.01) | |
| *A61K 36/185* | (2006.01) | |
| *A61K 36/88* | (2006.01) | |

(52) U.S. Cl.
CPC .......... *A61K 36/886* (2013.01); *A61K 35/644* (2013.01); *A61K 36/185* (2013.01); *A61K 36/23* (2013.01); *A61K 36/38* (2013.01); *A61K 36/77* (2013.01); *A61K 36/87* (2013.01); *A61K 36/88* (2013.01); *A61K 36/896* (2013.01)

(58) Field of Classification Search
None
See application file for complete search history.

(56) References Cited

U.S. PATENT DOCUMENTS

| 6,846,499 B2 * | 1/2005 | El Mogy ................ A61K 8/922 424/725 |
| 2004/0170712 A1 * | 9/2004 | Sadek El Mogy .... A61K 8/922 424/757 |
| 2011/0124573 A1 * | 5/2011 | Gupta .................... A61K 8/347 514/18.6 |

OTHER PUBLICATIONS

Li et al. (2011) J. Ethnopharmacology vol. 133, No. 2, pp. 543-550.*
Reddy et al. (2011) J. Amer. Acad. Dermatol. e127-e135.*
Cavanagh et al. (2005) The Lancet, vol. 366, pp. 1725-1735.*
Lipsky et al. (2004) Clinical Infectious Diseases, 39: 895-910.*
Singh et al. (2005) JAMA, vol. 293, No. 2, pp. 217-228.*
Website document entitled: "Lavender Oil, Lavender Flowers" (available at http://www.naturalcosmeticsupplies.com/lavender-oil.html). Downloaded from website Sep. 29, 2015.*
Website document entitled: "Tea Tree Essential Oil". (available at http://www.auracacia.com/auracacia/aclearn/eo_teatree.html). Downloaded from website Sep. 29, 2015.*
Int'l Search Report for PCT/IB2013/053190, four pages (dated Jul. 2013).
Written Opinion for PCT/IB2013/053190, four pages (dated Jul. 2013).
Li et al. "Prospective randomized controlled study of a Chinese herbal medicine compound Tangzu Yuyand Ointment for chronic diabetic foot ulcers: A preliminary report" *Journal of Ethnopharmacology*, vol. 133, No. 2, pp. 543-550 (Jan. 2011; epub Dec. 2010).
Reddy et al. "Common complementary and alternative therapies with potential use in dermatologic surgery: Risks and benefits" *Journal of the American Academy of Dermatology*, vol. 68, No. 4, pp. e127-e135 (Apr. 2013; epub Sep. 2011).

* cited by examiner

*Primary Examiner* — Russell G Fiebig
(74) *Attorney, Agent, or Firm* — Sterne, Kessler, Goldstein & Fox P.L.L.C.

(57) ABSTRACT

The present invention relates to compositions comprising substances of natural origin for use in the treatment or preventing the onset or the aggravation of diabetic foot ulcers.

18 Claims, 2 Drawing Sheets

COMPOSITIONS FOR THE TREATMENT OF CHRONIC ULCERS

Figure 1:

This application is the U.S. national phase of International Application No. PCT/IB2013/053190, filed 23 Apr. 2013, which designated the U.S. and claims priority to Italian Application No. RM2012A000174, filed 23 Apr. 2012; the entire contents of each of which are hereby incorporated by reference.

The present invention relates to compositions comprising substances of natural origin for use in the treatment or preventing the onset or the aggravation of diabetic foot ulcers.

STATE OF THE PRIOR ART

Diabetes is widely recognized as one of the main causes of death and disability worldwide. Diabetes has short- and long-term negative effects. Control of blood sugar levels is the best preventive treatment for decreasing and delaying long-term negative effects of diabetes, but this is not always possible and, depending on various factors, such as the duration of a high sugar level in blood, the patient's physiology and race and the seriousness of the disease, long-term adverse effects will appear.

Three important long-term adverse effects are retinopathy, nephropathy and neuropathy. Retinopathy affects the retina and causes loss of vision in the final stages of the illness. Nephropathy affects kidneys and causes their malfunctioning, whereas neuropathy causes loss of feeling in limbs, above all in feet. As a secondary negative effect, neuropathy of foot nerves causes the creation of chronic wounds (ulcers), often infected by bacteria and other opportunistic infections. The treatment of these wounds is usually unsuccessful and, often, gives rise to a partial or total amputation of the foot.

Among persons with diabetes, 15% will experience a foot ulcer in the course of their life, and about 14-24% of persons with a foot ulcer will require amputation. Therefore, it is not surprising that diabetes is the main non-traumatic cause of lower limb amputations. Notwithstanding several efforts to avoid amputation in the last decade, the incidence of lower limb amputation in persons with diabetes is on the increase.

According to Wagner classification, a distinction is drawn between five "stages" or "types" of diabetic foot ulcers:

STAGE or TYPE I
Superficial, uninfected (skin, subcutis)
STAGE or TYPE II
Deep, uninfected (tendons, muscles, bones)
STAGE or TYPE III
Deep, infected
STAGE or TYPE IV
Ischemic lesions (parcellar necrosis or toe gangrene)
STAGE or TYPE V
Extensive gangrene of the foot (radical surgery)

Among known methods for the treatment of chronic wounds such as diabetic ulcers there are hydrotherapy, ultrasound treatment, application of nitric oxide-releasing hydrogels and Hyperbaric Oxygen. However, the known treatments entail some drawbacks. A few of them are very costly and therefore not easily available, others have dosage regimens that are very painful to the patient. Very often, known treatments are not effective enough, as chronic wounds (ulcers) are characterized by a very high recurrence rate.

Therefore, an object of the present invention is to provide new compositions for the treatment and the preventing of chronic ulcers, in particular to avoid the formation of diabetic foot ulcers, which are effective (i.e., with a minimal risk of recurrence) and easy to administer.

SUMMARY OF THE INVENTION

It was surprisingly discovered that the topical application of compositions comprising beeswax, an extract of *Hypericum*, an extract of red grape vine, an extract of horse chestnut, an extract of *Centella*, an extract of butcher's broom, an extract of Aloe is an effective cure in the treatment or preventing the onset or the aggravation of diabetic foot ulcers (or sores). The selection of the components proved to be absolutely non-toxic and well-tolerated, and enabled to make a composition that exhibited a combination of emollient and curative effects, which proved effective in the cure and prevention of chronic wounds, like, e.g., diabetic foot ulcers.

Therefore, object of the present invention are compositions comprising beeswax, an extract of *Hypericum*, an extract of red grape vine, an extract of horse chestnut, an extract of *Centella*, an extract of butcher's broom, an extract of Aloe for use in the treatment or preventing the onset or the aggravation of diabetic foot ulcers. Still further advantages, as well as the features and the modes of employ of the present invention, will be made apparent in the following detailed description of some preferred embodiments thereof, given by way of example and not for limitative purposes. Reference will be made to the figures of the annexed drawings.

DETAILED DESCRIPTION OF THE FIGURES

FIG. 1. In FIG. 1 is reported the photo of the diabetic foot of a diabetic patient, age 73, whose degree of severity of the conditions predisposing to ulcers according to the assessment scheme reported in example 2 was 1, that is, very dry skin with open fissures at the heel level.

Figure 2:

FIG. 2. In FIG. 2 is reported the photo of the same diabetic foot of FIG. 1 after treatment with the composition of the present invention, the degree of severity of the cutaneous anomaly assigned after treatment according to the assessment scheme reported in Example 2 was 3 (therefore, a +2 improvement), i.e., very dry skin without fissures.

DETAILED DESCRIPTION OF THE INVENTION

The present invention refers to compositions for use in the treatment or preventing of chronic wounds, like e.g. diabetic foot ulcers.

Such a composition, thanks to its protective, emollient and curative effects, proves particularly effective in the cure, the prevention and the slowing down of the evolution of such chronic ulcers to more severe stages.

The composition also exerts on the concerned zone a barrier effect enabling to preserve the integrity of the skin hydrolipid film, indirectly causing the following effects:

moisturizing/emollient action
lenitive, anti-inflammatory action
microcirculation-improving action The barrier effect of the composition of the invention enables also the other components of the composition to remain adhered longer in contact on irritated skin, preventing a quick washing away thereof by biological fluids (suppurations, sweat), and therefore enables the composition to carry on its effect for a longer time and at best.

In an embodiment of the invention, the composition described herein is effective in the treatment of type-I diabetic foot ulcers, by promoting a regression from said stage, or slowing down the evolution or, relative to type-I ulcers, preventing the evolution from type-I ulcers to type-II ulcers.

The essential components of the composition, that is the active principles utilized, are beeswax, an extract of *Hypericum*, an extract of red grape vine, an extract of horse chestnut, an extract of *Centella*, an extract of butcher's broom, an extract of Aloe, to which there may be added other components as described below.

Extract of red grape vine; the species *Vitis vinifera* comprises a very large number of different species of vines; some of these, due to the peculiar leaf hue, are defined as "red grape vine". For preparing an extract of red grape vine according to the present invention, leaf-derived plant materials may be utilized. The extract may be prepared from at least one of the several varieties belonging to the species *Vitis vinifera* falling within the definition of red grape vine. Therefore, it is understood that, in the present description, the term "red grape vine" or "vine" has to be considered as denoting any one of the many varieties of plants belonging to the species *Vitis vinifera* commonly defined as "red grape vine".

The extract of red grape vine leaves contained in the composition could range from 0.01% to 2% of the total weight of the composition, like e.g. in an amount ranging from 0.05% and 0.2% of the total weight of the composition. The extract used in the composition could be, e.g., a lyophilized (freeze-dried) extract, a fluid extract, a glyceric extract, a glycolic extract.

Extract of horse chestnut (or *Aesculus hippocastanum*). The extract of horse chestnut could be used, e.g. in the form of dry extract of seeds. The extract of horse chestnut contained in the composition could range from 0.01% to 10% of the total weight of the composition, and preferably in an amount ranging from 0.2% and 1% of the total weight of the composition.

Beeswax is mainly comprised of myricin (myricyl palmitate and myricyl alcohol), cerotic acid and esters thereof, and high-Carbon paraffins, obtained from honey by centrifuging, used as emollient, emulsifier and filmogen in cosmetic formulations. Beeswax content in the composition could range from 0.01% to 7% of the total weight of the composition, and preferably in an amount comprised from 0.2% and 5% of the total weight of the composition. Yellow wax from *Apis mellifera* honeycomb could be used.

Extract of *Hypericum* could be an extract of perforate *Hypericum*, also known as St John's wort, is a species belonging to genus *Hypericum*, contains a large number of different classes of substances: naphtodianthrone derivatives, like hypericin, pseudohypericin and isohypericin, and phlorogucinol derivatives, like hyperforin. It also contains flavonoids, like hyperoside, rutin, quercetin, quercitrin and isoquercitrin, procyanidins, essential oils and xanthans.

For extract preparation, flowering tops were used as raw matter.

Of course, the extract may be prepared from at least one of the many varieties belonging to the species *Hypericum perforatum* (perforate *Hypericum*) Therefore, it is understood that, in the present description, the term "*Hypericum perforatum*" or "perforate *Hypericum*", or "*Hypericum*" should be construed as indicating any one of the many varieties of plants belonging to the species *Hypericum perforatum*.

The final extract could be prepared, e.g., in the form of dry, soft, lyophilized extract, preferably as oily extract according to the methods known in the state of the art. *Hypericum*, according to tradition, is an oily extract obtained by macerating flowering tops of fresh *Hypericum* in sunflower oil under sunlight. Exposure to the Sun enables to completely transform hypericin, and to increase the content of flavonoids in the oily solution, said flavonoids exerting an anti-oxidizing and lenitive action. Hypericin degradation products give to the oil its red-brown colour, whereas the chemical compound hyperforin seems to be accountable for the protective properties of the oil.

Dry plant extracts could be prepared by total evaporation of the solvent at temperatures lower than 50° C., preferably lower than 40° C. so as not to alter active principles.

The extract of *Hypericum* contained in the composition could range from 3% to 10% of the total weight of the composition, and preferably in an amount comprised between 5% and 6% of the total weight of the composition.

In all cases in which the use of plant oil is indicated above for preparing the extracts, such oil could also be in the form of emulsion: oil in water, water in oil or also oil in gel or gel in oil.

Extract of Aloe. In the compositions, the extract of any plant of genus Aloe could be used; preferably, extracts of Aloe vera (or Aloe Barbadensis Miller) plant will be used. Aloe gel is contained in the parenchym of the fresh leaf of Aloe vera plant. By an atomization drying process, a product with a particularly high concentration of polysaccharides (on average, 200-fold with respect to leaf-extracted gel) is obtained. Aloe polysaccharides are comprised of glucose, mannose and glucomannan monomers.

Aloe gel can form protective films on the tissues (both mucosal and cutaneous).

In an in vitro study, the ability of polysaccharide and flavonoid components of aloe gel to protect linoleic acid from peroxidation was demonstrated. The presence of an extract of Aloe inside the pomade contributes to the performing of the effect of protection and of restoring skin integrity.

The extract, like e.g. the dry extract of foliar gel, could be obtained from leaves as known in the state of the art. The extract of Aloe contained in the composition could range from 0.01% to 3% of the total weight of the composition, and preferably in an amount comprised from 0.1% and 0.5% of the total weight of the composition.

Extract of butcher's broom contains various compounds, like sapogenins (ruscogenins), phytosterols, fatty acids, simple and complex sugars, a small amount of essential oil, tannins and flavonoids. The extract of butcher's broom utilized could be, e.g., in the form of a lyophilized extract, a fluid extract, a glyceric extract, a glycolic extract. Specific studies performed by the Inventors highlighted the presence, in the freeze-dried extract of Butcher's broom, of polysaccharides having a high molecular weight (>25000 Daltons) in a good concentration. These act synergistically with Aloe ones, potentiating their abilities to form a protective film.

The extract of butcher's broom contained in the composition could range from 0.01% to 5% of the total weight of the composition, and preferably in an amount comprised from 0.5% and 1.2% of the total weight of the composition.

Extract of *Centella*. In the compositions, the extract of any plant of genus *Centella* could be used; preferably, lyophilized extracts obtained from *Centella asiatica* leaves will be used. The extract of *Centella* contained in the composition could range from 0.01% to 5% of the total weight of the composition, and preferably in an amount comprised from 0.1% and 1% of the total weight of the composition.

The compositions of the present invention could further comprise other plant components with beneficial effects, like e.g. oils having an indirect moisturizing effect, like e.g. jojoba oil or the like.

Jojoba oil. Jojoba oil is a "liquid wax"-like oil produced from the seed of jojoba (or *Simmondsia chinensis*) plant, obtained by a cold pressing process of fresh seeds. It is essentially comprised of a mixture of esters of long-chain (C40 and C44) fatty acids with fatty alcohols and without glycerol molecules. It is very stable, does not oxidize and does not go rancid even after repeated heat treatments. Jojoba oil restores the cutaneous lipid barrier, ensuring a very good non-occlusive emollient effect and an indirect moisturizing effect. It is easily absorbed by the skin, because it made of small molecules having a linear structure with a relatively high polarity and because it has a high affinity for sebum, thanks to the presence of fatty acids similar to those present in the lipid film. Oil constitutes about the 50% of jojoba seeds by weight and can be extracted from the seed according to techniques of oil extraction from seed, known in the state of the art.

Jojoba oil contained in the composition could range from 2% to 12% of the total weight of the composition, and preferably in an amount comprised from 6% and 8% of the total weight of the composition.

The compositions could also comprise one or more perfuming and/or colouring agents, like for instance essential oils selected from: lavender essential oil, *melaleuca* essential oil, peppermint essential oil, lemon, rose wood, cypress. The addition of these agents confers to the compositions the further advantage of perfuming the zone concerned by the wound (ulcer) and/or of colouring the composition.

Of course, there are comprised also the decimal numbers between each integer of the ranges afore-indicated in the present description.

The composition could be in the form of gel, ointment, cream, pomade, foam, powder, emulsion oil in water, emulsion water in oil, emulsion oil in gel or emulsion gel in oil, or any other composition suitable for topical administration. An emulsion "oil in water" is defined as an emulsion in which the dispersing phase is of aqueous type and the dispersed phase is of oily type, whereas otherwise it is referred to as emulsion water in oil.

The composition could further contain one or more among carriers, diluents, excipients, emulsifiers, emollients, preservatives, consistency factors, pH adjusters, antioxidants (like, e.g., vitamins, tocopherols or other antioxidants known in the field), suitable for the making of formulations for topical use (pharmaceutical ones or medical devices) like e.g. or more glycerol, xanthan gum, potassium sorbate, sodium silicate, cetearyl glucoside, cetearyl alcohol, cetyl stearyl alcohol, hydrogenated castor oil, glycerol monostearates, dicaprylyl carbonate, citric acid, stearic acid, dimethicone, triethanolamine, urea, glyceryl oleate, carbomer.

Such compositions could be prepared according to the techniques known to the technician in the field by utilizing the above-described compounds, e.g. by mixing the individual compounds directly during the preparing of the composition, or by adding to the carriers and/or diluents and/or excipients a mixture of the compounds previously prepared.

The composition according to the present description could be made in the form of a pharmaceutical composition or of a medical device according to any one of the classes described in the Medical Devices Directive 93/42/EEC (comprising also substances and not only "devices" in the mechanical sense of the term), or in any other form according to the regulatory provisions of the Country in which said composition will be produced.

When made in the form of a pharmaceutical composition, the components utilized, as well as the excipients, will be of a grade pharmaceutically acceptable for the desired use (topical, in this case). Such grade could be utilized also for the components and excipients for the preparing of the composition as a medical device or of the composition comprised in a medical device.

In an embodiment the medical device could be a medicated patch, a medicated gauze or a medicated bandage to be applied on the area concerned by the wound (ulcer). By the term "medicated" in the present description it is meant that the patch, gauze or bandage comprise the compositions according to the present invention, e.g. a gauze soaked of a pomade, ointment or cream.

The present description provides also a method for the treatment and preventing of chronic wounds, in particular of diabetic foot ulcers, comprising the topical administration, to patients in need thereof, of effective amounts of a composition as described herein.

According to a non-limiting example of the method for the treatment described herein, the composition according to the invention could be administered once or more per day, by local (topical) application on the parts to be treated for a time period of 3 to 6 weeks, or even longer.

COMPOSITION EXAMPLES

According to non-limiting embodiments, the composition of the invention could contain the above-described active components in percents by weight as those reported below; the remaining components will be agents suitable to the making of the desired final form, which could be, e.g., like: emulsion oil in water, emulsion water in oil, emulsion oil in gel or emulsion gel in oil, multiple emulsions, sprays, and anhydrous formulations (pomade, gel, paste, cream, ointment). Some of these agents are reported hereinafter as "examples of possible embodiment", but are to be understood as replaceable with other agents having a similar activity, commonly used by the technician in the field, or with mere carriers. To be more precise, may we remind that the active principles that must always be present in the composition of the invention are beeswax, an extract of *Hypericum*, an extract of red grape vine, an extract of horse chestnut, an extract of *Centella*, an extract of butcher's broom, an extract of Aloe, and such components are the essential ones also in the composition examples reported below.

The abbreviation "le" signifies "lyophilized extract"

The percents reported hereinafter are to be understood as percents by weight with respect to the total weight of the composition. The remainder, q.s., to 100%, will be comprised of suitable excipients, of which, normally, mostly water.

Example 1

| | |
|---|---|
| Red grape vine, le | 0.05-4% |
| Horse chestnut, le | 0.2-1% |
| *Centella*, le | 0.1-1% |
| Butcher's broom, le | 0.2-1.2% |

-continued

| Aloe, dry extract | 0.1-0.5% |
| --- | --- |
| Beeswax | 0.2-1% |
| *Hypericum* oil | 5-6% |
| Cetearyl glucoside | 2-6% |
| Cetyl stearyl alcohol | 0.5-10% |
| Xanthan gum | 0.01-1% |
| Potassium sorbate | 0.01-1% |
| Benzyl alcohol | 0.01-2% |
| Dicaprylyl carbonate | 0.5-10% |
| Deionized water | 20-70% |
| Jojoba oil | 6-8% |
| Peppermint essential oil | 0.01-2% |

Example 2

| Beeswax | 0.1-1% |
| --- | --- |
| *Hypericum* oil | 6-8% |
| Red grape vine, le | 0.05-2% |
| Horse chestnut, le | 0.2-1% |
| *Centella*, le | 0.1-0.5% |
| Butcher's broom, le | 0.5-1.2% |
| Aloe, dry extract | 0.1-0.5% |
| Jojoba oil | 6-8% |
| Peppermint, essential oil | 0.2-0.6% |
| *Melaleuca*, essential oil | 0.2-0.6% |

The composition according to the present invention could be prepared by mixing, by conventional techniques, the active components according to the detailed description and optional additional components as above-indicated, and appropriate agents suitable for preparing compositions for topical use, up (q.s.) to 100% of the composition. Such agents could be, e.g., carriers, diluents, emulsifiers, emollients, preservatives, antioxidants. No specific preparation protocols are needed, since conventional protocols are suitable for making the composition in any form indicated in the present description.

In the examples provided above, as additional components (Carriers, diluents, emulsifiers, emollients, preservatives, antioxidants) to the active principles indicated in the text there are utilized: Cetearyl glucoside, Cetyl stearyl alcohol, Xanthan gum, Potassium sorbate, Benzyl alcohol, Dicaprylyl carbonate, Jojoba oil, Peppermint essential oil, Deionized water q.s. to 100%, for example 1, and Jojoba oil, Peppermint essential oil, Deionized water q.s. to 100%, for example 2.

It is evident that the composition according to the invention could comprise further carriers, diluents, emulsifiers, emollients, preservatives, antioxidants suitable for the formulation, which will be represented mostly by water, like e.g. deionized water and/or demineralized water, optionally sterilized, and one or more from cetearyl alcohol, cetearyl glucoside, gliceryl monostearate, behenyl alcohol, sodium stearoyl glutammate, cetyl stearyl alcohol, caprilyl carbonate, caprylic/capric triglycerid, tocopherols, sodium dehydroacetate, citric acid, glycerol, xanthan gum, potassium sorbate, sodium silicate, benzyl alcohol.

Preferably, water will represent from 50 to 60% by weight of the composition. Hereinafter, examples, preparation and experimental results obtained with the composition described herein are provided.

The preparation examples are not limitative of the present description but serve to exemplify some of the possible embodiments thereof.

Examples and Experimental Results

Example 1

Preparation of the Pomade of Composition Example 1

In a vessel of suitable size, the lipophilic phase consists of the oils, the emulsifiers, the consistency factors and the liposoluble active agents was brought to a temperature of 70-75° C., under stirring.

In a vessel of suitable size, the hydrophilic phase consists of the water, the rheological additives and the hydrosoluble active agents, was brought to a temperature of 70-75° C., under stirring.

Upon reaching the temperature, the two phases were joined under vacuum and under stirring. The whole was cooled and thermolabile components, like e.g. preservatives and essential oils, were added, always under suitable stirring.

Example 2

Studies Related to Administration of the Pomade of Composition Example 1 on Patients Suffering from Diabetic Foot Study and Data Collection 38 informed patients with diabetic foot ulcers were recruited. For each patient, a photographic documentation of the cutaneous zones of the foot concerned by ulcers prior to the treatment was produced, and a value was assigned on the basis of ulcer severity, according to the assessment scheme reported hereinafter:

1) very dry, with open fissures at the heel level
2) very dry, with closed fissures of the heel
3) very dry, without fissures
4) moderately dry
5) healthy, but with zones of slight dryness in the pressure zones
6) healthy and hydrated It appears that the prevailing feature in diabetic foot conditions is skin dehydration, a feature present in all conditions 1 to 5.

The patients were then divided into two homogeneous groups, each one consisting of 19 patients. The first group was treated for one month with the composition of the invention. The second group was treated for the same period with a commercially available composition having a "barrier" and protective action, containing oily extract of *Hypericum* and jojoba oil and foliar gel of Aloe vera. At the end of the treatment, the concerned zones of the foot were again photographed, and the values reassigned according to the same assessment scheme. Hereinafter, the results obtained at the end of the treatment are reported.

The assessment values of each patient belonging to the group were added up before treatment, and this total was checked with the sum of the assessment values of each patient belonging to the group after treatment, in order to obtain an overall data on the foot skin condition pattern in the examined group.

Results obtained with the composition of the invention

PATIENTS EXAMINED: 19

NUMERICAL TOTAL AT THE START: 45 (Condition average: 2.36)

FINAL NUMERICAL VALUE AFTER TREATMENT: 91

INCREASE: +46

Therefore, an "average foot condition value" of about 2.36 was turned into an average condition value of about 4.78.

Results obtained with the composition having a barrier/protective effect

PATIENTS EXAMINED: 19

NUMERICAL TOTAL AT THE START: 48

FINAL NUMERICAL VALUE: 61

INCREASE: +13

Therefore, "an average foot condition value" of about 2.5 was turned into an average condition value of about 3.2.

It appears evident that the group treated with the composition of the invention has an improvement about 3 times greater than the group treated with the commercial compound, in spite of said compound sharing some active ingredients with the composition described herein. Evidently, the presence of the combination of active ingredients selected by the Inventors represents a clear improvement with respect to the state of the art, 3. Comparative Barrier Effect Test As explained in the introductive part of the application, the composition of the invention proved to be absolutely non-toxic and well-tolerated, and enabled to make a composition that exhibited a combination of emollient and curative effects, that proved effective in the cure and prevention of chronic wounds, such as, e.g., diabetic foot ulcers. Its barrier effect enables to preserve the integrity of the cutaneous hydrolipid film by exerting a protective action, and enables also the other components of the composition to remain adhered for a longer time into contact on the irritated skin, preventing a quick washing off thereof by biological fluids (suppurations, sweat), thereby enabling the composition to carry on its effect for a longer time and at best.

Then, there were assessed the barrier effect of the composition as claimed in claim 1 and as exemplified in the composition Example 1 and 2, and therefore comprising as active principles beeswax, an extract of *Hypericum*, an extract of red grape vine, an extract of horse chestnut, an extract of *Centella*, an extract of butcher's broom, an extract of Aloe, and, in parallel, the effect of the composition stripped of each one of its components.

The data reported below prove how the combination of the components selected by the Inventors carries out a very high barrier effect with respect to the composition lacking any one of the components.

Assessment tests were carried out as follows, by a method developed for simulating in vitro the protective action of substances and formulations that, applied on skin and mucosae in vivo, form an "insulating" film against environmental agents.

The design exploits the principle due to which cells subjected to contact with an inflammatory agent produce and secrete pro-inflammatory mediators (cytokines) into the extracellular environment in an amount correlated to the degree of inflammation caused. The greater the amount of inflammatory agent that reaches the cells, the greater the amount of cytokines released.

The design provides the setting up of two chambers, physically separated by a semipermeable membrane allowing transit of sufficiently small solutes.

In the bottom chamber, comprised of a well containing cell culture plates, HuDe cells (Number BS PRC 41, purchased from the Zooprophylactic Institute of Brescia) are grown, whereas the top chamber, comprised of an insert for complex cell cultures (transwells), houses the inflammatory agent.

Onto the surface of the semipermeable membrane of the insert separating the two chambers, prior to the inletting of the inflammatory agent into the top chamber, a thin film of the sample under analysis is arranged in layers in order to assess any barrier effect (BE) thereof to the free transit of the inflammatory agent.

Depending on the insulating abilities of the sample, a decrease in the migration of the inflammatory agent from the top chamber and, accordingly, a lesser stimulation of the cells to cytokines production will be had. The extent of the inflammatory reaction is assessed through the semiquantitative dosage of cytokines released in the culture medium of the bottom chamber, in particular of interleukin 6 (IL-6).

An analogous experiment in which no sample is arranged in layers on the membrane is used as control, thereby enabling to measure the effect of the inflammatory agent without any barrier apart from the semipermeable membrane.

Moreover, an internal control is utilized in which culture cells are pre-treated with the substance apt to induce marker release, and the sample is located on the semipermeable membrane in the absence of said substance, then one or more measurements of the amount of marker in the culture medium of said internal control are carried out. In the internal control, therefore, first the cells are stimulated with the inducing substance and then it is checked whether the sample, possibly crossing the membrane and passing into the cells urged by the above medium, has any effect of marker release reduction not related to the barrier effect. For instance, when an inflammatory agent is used as inducing substance the internal control enables to understand if the decrease in cytokines concentration in the culture medium is due to the barrier effect, or if the sample possibly passing into the cells urged by the above medium has any effect of inflammatory response reduction independently of the barrier effect.

Barrier effect (BE) is expressed as percent of IL-6 release reduction, and is obtained by comparison with the positive control in which the two chambers are separated by the same type or semipermeable membrane without the barrier created by the sample.

4.1 Cell Culture Preparation:

For each sample tested, HuDe line cells were seeded into the wells of a culture cell plate, one for the Barrier Test (B.T.) and another one for the internal control at the density of 40.000 cells/ml in MEM medium completed with 10% bovine serum (FBS); 1 ml of cell suspension per well.

Cells were treated with SAMPLE (SAM), with the POSITIVE CONTROL (C+) (inflammatory agent w/o sample), and with the NEGATIVE CONTROL (C−) (medium only). Each test was carried out in triplicate.

Plates were incubated at 37° C. overnight (22-24 hours).

4.2 Preparation of Complex Cell Culture Inserts

Complex cell culture inserts (Cell Culture Inserts (Becton Dickinson)) were positioned on other plates, and onto each of them a set amount of collagen, 0.1 mg/ml, was dispensed. Plates were incubated at 37° C. overnight (22-24 hours).

Day 2

4.3 Checking Cell Confluence State and Level

In order to proceed with the test, a ≥5% confluence was required.

4.4 Collagen Layer Drying

From the two plates (B.T. and I.C.) with the inserts collagen is removed, and the inserts are left under hood flow for the time required to dry them completely (10÷15 minutes).

4.5 Barrier Test (B.T.)

The steps described hereinafter are performed in the culture plate for the B.T.

Setting Up the Sample Layer in the B.T.:

Onto the semipermeable membrane of the sample, 100 μl of a 0.5% alginate-based composition were inoculated and left to stratify for 20 min, while nothing was added into the C+ and C− inserts. When the 20 min had elapsed, excess sample was disposed of and a membrane washing with PBS was performed according to modes specified by the protocol.

LPS (Inflammatory Agent) Addition to BT Inserts

Once sample layers had dried, into the first three CAM inserts and into the three C+ ones 300 μl of the LPS (membrane lipopolysaccharide) were inoculated at a concentration of 1 μg/ml, whereas into the remaining three of the C− 300 μl of 5% FBS MEM were added. The inserts were inserted into the respective wells, with the cells and plates incubated for 1 h at 37° C. and under 5% $CO_2$-enriched atmosphere overnight (22-24 hours).

Once 1 h of incubation had elapsed, the inserts were removed and discarded and the plates put back to incubate overnight (22-24 hours).

4.6 Internal Control (I.C.) Test:

The internal control test was performed concomitantly with the BT.

I.C. Cells Exposure to LPS:

Once dry, into the first six inserts of the I.C., three for the sample to be analyzed, CAM, and three for the C+, 300 μl of LPS solution were inoculated, whereas in the remaining three ones of the C− 300 μl of medium were added.

The inserts with LPS and MEM were then inserted into the wells with the I.C. cells, and the whole was put away to incubate for 1 h.

LPS Removal and I.C. Membranes Drying:

Once 1 hour of incubation had elapsed, inserts were removed from wells with cells and transferred into the empty plate, whereas the plate with cells was put away in the incubator.

LPS solution still present was removed from the inserts, these were subjected to a rapid washing with sterile ultra-pure water and left to dry.

Setting Up of a Sample Layer in the I.C.:

On the semipermeable membrane of the three inserts for the sample, 100 μl of a 0.5% alginate-based composition were inoculated and left to stratify for 20 minutes, whereas nothing was added into the C+ and C− inserts. Once 20 minutes had elapsed, excess sample was removed and a membrane washing with PBS was carried out according to modes specified by the protocol.

LPS Addition to I.C. Inserts

Once the inserts with the samples were ready, 300 μl of medium were added into all inserts (CAM, C+C−). The inserts were inserted into the respective wells with cells, and the plates put to incubate for 1 h at 37° C.

Once 1 hour of incubation had elapsed, inserts were removed and discarded and the plates put back to incubate overnight (22-24 hours).

Day 3

4.7 Supernatant Collection and Immunoenzymatics

Once 22-24 h had elapsed, supernatants were collected from B.T. and I.C. plates for carrying out ELISA test and semiquantitative IL-6 dosage.

Barrier Effect (BE) Assessment

The BE of a substance or compound is expressed as % of reduction of IL-6 cytokine release by cells exposed to LPS in which the sample was tested, relative to the positive control (C+) in which cells were exposed only to LPS.

BE=% of reduction of IL-6 cytokine release=100−
[(pg/μL cytokines released from sample/pg/μL cytokines released from C+)×100]

Table 1 reported below shows the various formulations of the tested compositions, in which A is the formulation according to claim 1, composition example 1 (comparable data were obtained with the formulation example 2), whereas compositions A1 to A9 correspond to formulation A stripped, each time, of an active ingredient replaced by water.

A1=A-beeswax
A2=A-*Hypericum*
A3=A-Red grape vine
A4=A-Horse chestnut
A5=A-*Centella asiatica*
A6=A-butcher's broom
A7=A-Aloe

TABLE 1

| | FORMULA A | FORMULA A1 | FORMULA A2 | FORMULA A3 | FORMULA A4 | FORMULA A5 | FORMULA A6 | FORMULA A7 |
|---|---|---|---|---|---|---|---|---|
| ACTIVE PRINCIPLES % | | | | | | | | |
| ORGANIC BEESWAX | 0.5 | 0 | 0.5 | 0.5 | 0.5 | 0.5 | 0.5 | 0.5 |
| *HYPERICUM* OIL | 7 | 7 | 0 | 7 | 7 | 7 | 7 | 7 |
| RED GRAPEVINE, EL | 0.1 | 0.1 | 0.1 | 0 | 0.1 | 0.1 | 0.1 | 0.1 |
| HORSE CHESTNUT, EL | 0.5 | 0.5 | 0.5 | 0.5 | 0 | 0.5 | 0.5 | 0.5 |
| *CENTELLA*, EL | 0.2 | 0.2 | 0.2 | 0.2 | 0.2 | 0 | 0.2 | 0.2 |
| BUTCHER'S BROOM, EL | 0.8 | 0.8 | 0.8 | 0.8 | 0.8 | 0.8 | 0 | 0.8 |
| ALOE, DRY EXTRACT | 0.2 | 0.2 | 0.2 | 0.2 | 0.2 | 0.2 | 0.2 | 0 |

TABLE 1-continued

| | FORMULA A | FORMULA A1 | FORMULA A2 | FORMULA A3 | FORMULA A4 | FORMULA A5 | FORMULA A6 | FORMULA A7 |
|---|---|---|---|---|---|---|---|---|
| JOJOBA OIL | 7 | 7 | 7 | 7 | 7 | 7 | 7 | 7 |
| PEPPERMINT, ESSENTIAL OIL | 0.5 | 0.5 | 0.5 | 0.5 | 0.5 | 0.5 | 0.5 | 0.5 |
| *MELALEUCA*, ESSENTIAL OIL | 0.5 | 0.5 | 0.5 | 0.5 | 0.5 | 0.5 | 0.5 | 0.5 |
| EXCIPIENTS % Citric acid, benzyl alcohol, Dicapryl carbonate, Cetearyl alcohol, Cetearyl glucoside, glyceryl stearate, stearoyl-glutammate, caprylic/capric triglycerides, seed oil of *Heliantus annuus*, tocopherol, sodium dehydroacetate, glycerol, xanthan gum, potassium sorbate, sodium silicate | 26.1 | 26.1 | 26.1 | 26.1 | 26.1 | 26.1 | 26.1 | 26.1 |
| DEIONIZED WATER | Q.S. TO 100 | Q.S. TO 100 | Q.S. TO 100 | Q.S. TO 100 | Q.S. TO 100 | Q.S. TO 100 | Q.S. TO 100 | Q.S. TO 100 |

The obtained data, reported in Table 2 below, show how all samples tested (that is, the composition as claimed in claim 1 stripped of a component) prove to have more or less markedly a barrier effect.

The results highlight, in particular, that the barrier effect by far most effective (IL-6 cytokine release inhibition equal to 82%) is observed with the composition of the invention, compared to all other formulations in which one of the components of the complete formulation is absent.

TABLE 2

| NET BARRIER EFFECT | % IL-6 CYTOKINE RELEASE INHIBITION |
|---|---|
| 1) Composition A (claimed composition) | 82 |
| 2) Composition A1 (composition A lacking organic beeswax) | 46 |
| 3) Composition A2 (composition lacking *Hypericum* oil) | 36 |
| 4) Composition A3 (composition lacking Red grape vine LE) | 64 |
| 5) Composition A4 (composition A lacking Horse chestnut LE) | 33 |
| 6) Composition A5 (composition A lacking *Centella* LE) | 65 |
| 7) Composition A6 (composition A lacking butchers broom LE) | 57 |
| 8) Composition A7 (composition A lacking Aloe dry extract) | 20 |

The invention claimed is:

1. A pharmaceutical composition for topical treatment of chronic ulcers, the composition comprising: beeswax at a concentration of 0.1%-1% by weight, an extract of *Hypericum* at a concentration of 6%-8% by weight, an extract of red grape vine at a concentration of 0.05%-2% by weight, an extract of horse chestnut at a concentration of 0.02%-1% by weight, an extract of *Centella* at a concentration of 0.1%-0.5% by weight, an extract of butcher's broom at a concentration of 0.5%-1.2% by weight, an extract of Aloe at a concentration of 0.1%-0.5% by weight, jojoba oil at a concentration of 6-8% by weight, peppermint essential oil at a concentration of 0.2-0.6% by weight, and *melaleuca* essential oil at a concentration of 0.2-0.6% by weight.

2. The composition according to claim 1, further comprising one or more perfuming and/or coloring agents.

3. The composition according to claim 2, wherein said one or more perfuming agents are essential oils selected from the group consisting of: lavender essential oil, and peppermint essential oil.

4. The composition according to claim 1, wherein said extract of *Centella* is an oily extract of leaves of *Centella asiatica*.

5. The composition according to claim 1, wherein said extract of *Hypericum* is an oily extract of flowers and/or leaves and/or stems.

6. The composition according to claim 1, wherein said jojoba oil is seed oil.

7. The composition according to claim 1, wherein said beeswax is yellow wax from *Apis mellifera* honeycomb.

8. The composition according to claim 1, wherein said Aloe extract is a dry foliar gel oil.

9. The composition according to claim 1 in the form of gel, ointment, cream, pomade, foam, powder, spray, emulsion oil in water, emulsion water in oil, emulsion oil in gel, emulsion gel in oil, or suspension.

10. A medical device comprising the composition according to claim 1.

11. The medical device according to claim 10 in the form of medicated patch, medicated gauze, or medicated bandage.

12. A method for treating diabetic foot ulcers, the method comprising: topically applying an effective amount of the composition of claim 1 to a patient in need thereof.

13. The method according to claim 12, wherein said diabetic foot ulcers are diabetic foot ulcers of the first grade.

14. The method according to claim 12, wherein said composition is administered once or more per day.

15. The method according to claim 14, wherein said composition is locally applied for a time period from three weeks to six weeks.

16. A method for treating a diabetic patient having a foot ulcer, the method comprising: topically applying an effective amount of the composition of claim 1 to a patient in need thereof.

17. A pharmaceutical composition for topical treatment of chronic ulcers, the composition comprising beeswax at a concentration of 0.5% by weight, an extract of *Hypericum* at a concentration of 7% by weight, an extract of red grape vine at a concentration of 0.1% by weight, an extract of horse chestnut at a concentration of 0.5% by weight, an extract of *Centella* at a concentration of 0.2% by weight, an extract of butcher's broom at a concentration of 0.8% by weight, an extract of Aloe at a concentration of 0.2% by weight, jojoba oil at a concentration of 7% by weight, peppermint essential oil at a concentration of 0.5% by weight, and *melaleuca* essential oil at a concentration of 0.5% by weight.

18. A method for treating a diabetic patient having a foot ulcer, the method comprising: topically applying an effective amount of the composition of claim 17 to a patient in need thereof.

* * * * *